US012797342B2

(12) United States Patent
Ishibashi et al.

(10) Patent No.: US 12,797,342 B2
(45) Date of Patent: Nov. 17, 2026

(54) LIDOCAINE-CONTAINING PATCH

(71) Applicant: MEDRx Co., Ltd., Kagawa (JP)

(72) Inventors: Masaki Ishibashi, Higashikagawa (JP); Hidetoshi Hamamoto, Higashikagawa (JP)

(73) Assignee: MEDRx Co., Ltd., Kagawa (JP)

( * ) Notice: Subject to any disclaimer, the term of this patent is extended or adjusted under 35 U.S.C. 154(b) by 0 days.

(21) Appl. No.: 17/263,726

(22) PCT Filed: Apr. 20, 2020

(86) PCT No.: PCT/JP2020/017075
§ 371 (c)(1),
(2) Date: Jan. 27, 2021

(87) PCT Pub. No.: WO2020/218249
PCT Pub. Date: Oct. 29, 2020

(65) Prior Publication Data

US 2021/0369636 A1 Dec. 2, 2021

(30) Foreign Application Priority Data

Apr. 24, 2019 (JP) ................................ 2019-082678
Jul. 1, 2019 (JP) ................................ 2019-122757

(51) Int. Cl.
*A61K 9/70* (2006.01)
*A61K 31/167* (2006.01)
*A61K 47/12* (2006.01)
*A61K 47/14* (2017.01)

(52) U.S. Cl.
CPC .......... *A61K 9/7053* (2013.01); *A61K 31/167* (2013.01); *A61K 47/12* (2013.01); *A61K 47/14* (2013.01)

(58) Field of Classification Search
CPC .... A61K 9/7053; A61K 31/167; A61K 47/12; A61K 47/14; A61K 9/7046; A61P 23/02
See application file for complete search history.

(56) References Cited

U.S. PATENT DOCUMENTS 4,814,168 A * 3/1989 Sablotsky ............ A61K 9/7076 424/448
5,124,157 A 6/1992 Colley et al.
5,420,106 A * 5/1995 Parab ...................... A61P 17/00 424/443
8,834,927 B2 9/2014 Sundberg et al.
9,168,232 B2 10/2015 Kawamura et al.
2004/0142024 A1* 7/2004 Chono ...................... A61P 1/08 424/449
2007/0065390 A1* 3/2007 Spengler ................ A61K 8/673 424/70.21
2010/0234471 A1 9/2010 Ishibashi et al.
2011/0152377 A1 6/2011 Hanma et al.
2012/0226245 A1 9/2012 Kawamura et al.
2013/0138057 A1 5/2013 Shirai et al.
2013/0224262 A1 8/2013 Akazawa et al.
2014/0037710 A1* 2/2014 Hashimoto .......... A61K 9/7053 424/443
2014/0141056 A1* 5/2014 Kubo .................. A61K 9/7046 424/443
2014/0302118 A1 10/2014 Kawamura et al.
2014/0356412 A1 12/2014 Mori et al.
2015/0098981 A1 4/2015 Pongpeerapat et al.
2016/0310441 A1 10/2016 Yamazaki et al.
2018/0177742 A1 6/2018 Mori et al.
2019/0209485 A1 7/2019 Hagiwara et al.
2020/0085770 A1 3/2020 Ishibashi et al.

FOREIGN PATENT DOCUMENTS

| | | | |
|---|---|---|---|
| CN | 109316469 | A | 2/2019 |
| EA | 023396 | B1 | 5/2016 |
| JP | H09-110680 | A | 4/1997 |
| JP | 2001-302501 | A | 10/2001 |
| JP | 2012-036170 | A | 2/2012 |
| JP | 2016-003196 | A | 1/2016 |
| JP | 2016-014052 | A | 1/2016 |
| RU | 2543639 | C2 | 3/2015 |
| WO | 2009/060629 | A1 | 5/2009 |
| WO | 2010/016219 | A1 | 2/2010 |
| WO | 2011/027786 | A1 | 3/2011 |
| WO | 2011/118604 | A1 | 9/2011 |
| WO | 2012/029097 | A1 | 3/2012 |
| WO | 2013/027840 | A1 | 2/2013 |
| WO | 2013/046335 | A1 | 4/2013 |
| WO | 2017/034041 | A1 | 3/2017 |
| WO | 2018/052039 | A1 | 3/2018 |
| WO | 2018/230687 | A1 | 12/2018 |

OTHER PUBLICATIONS

International Preliminary Report on Patentability and Written Opinion issued in corresponding International Patent Application No. PCT/JP2020/017075 dated Nov. 4, 2021.
International Search Report issued in corresponding International Patent Application No. PCT/JP2020/017075 dated Jun. 30, 2020.
Extended European Search Report issued in corresponding European Patent Application No. 20795974.3 dated Jan. 3, 2023.
Office Action and Search Report issued in corresponding Russian Patent Application No. 2021134123 dated Oct. 4, 2023.

* cited by examiner

*Primary Examiner* — Sarah Alawadi
*Assistant Examiner* — Thurman Wheeler
(74) *Attorney, Agent, or Firm* — Morgan, Lewis & Bockius LLP

(57) ABSTRACT

The present invention provides a patch preparation comprising lidocaine or a salt thereof, lactic acid, and a hydroxy acid having 4 to 6 carbon atoms, wherein the amount of lactic acid is 0.6 to 1.2 moles per mole of lidocaine or a salt thereof with high safety which can continuously produce the therapeutic effect of lidocaine for a long time by adjusting the skin penetration rate of lidocaine to a proper range when applied to the skin and also show the similar bioequivalence to the existing preparations comprising lidocaine even when high concentration of lidocaine is used.

13 Claims, 4 Drawing Sheets

[Fig. 1]
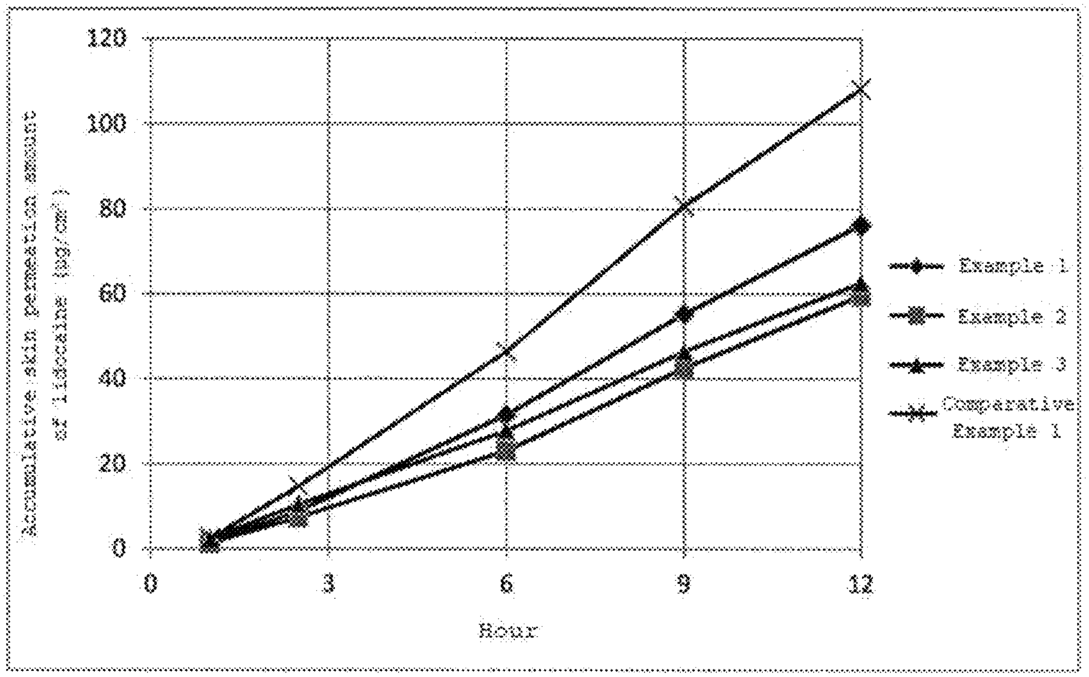
[Fig. 2]
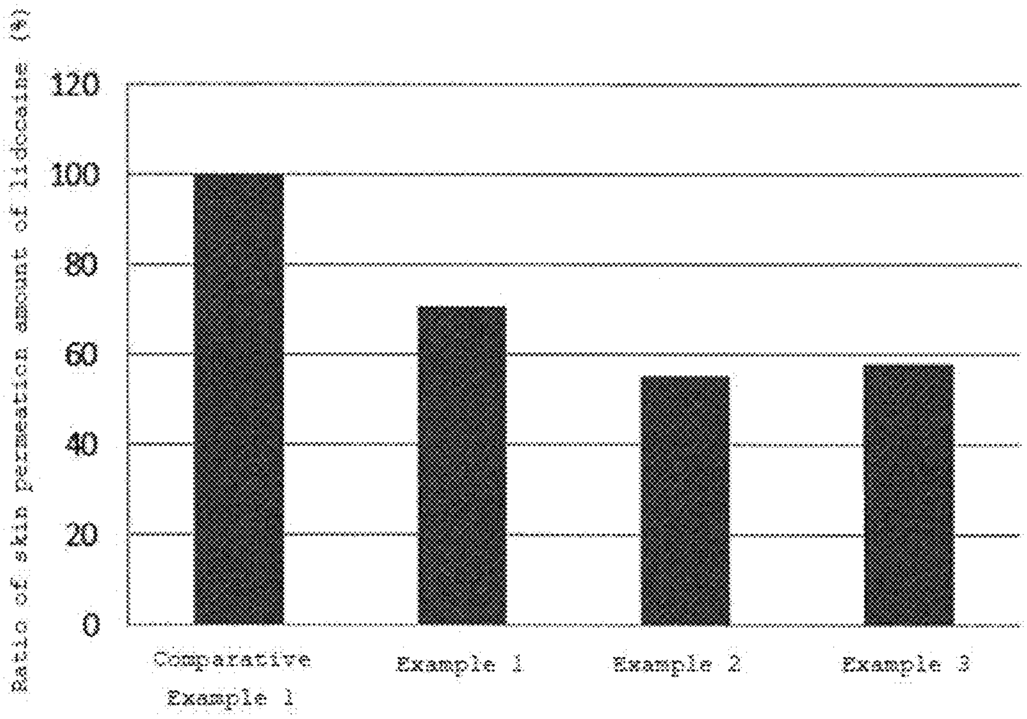

[Fig. 3]
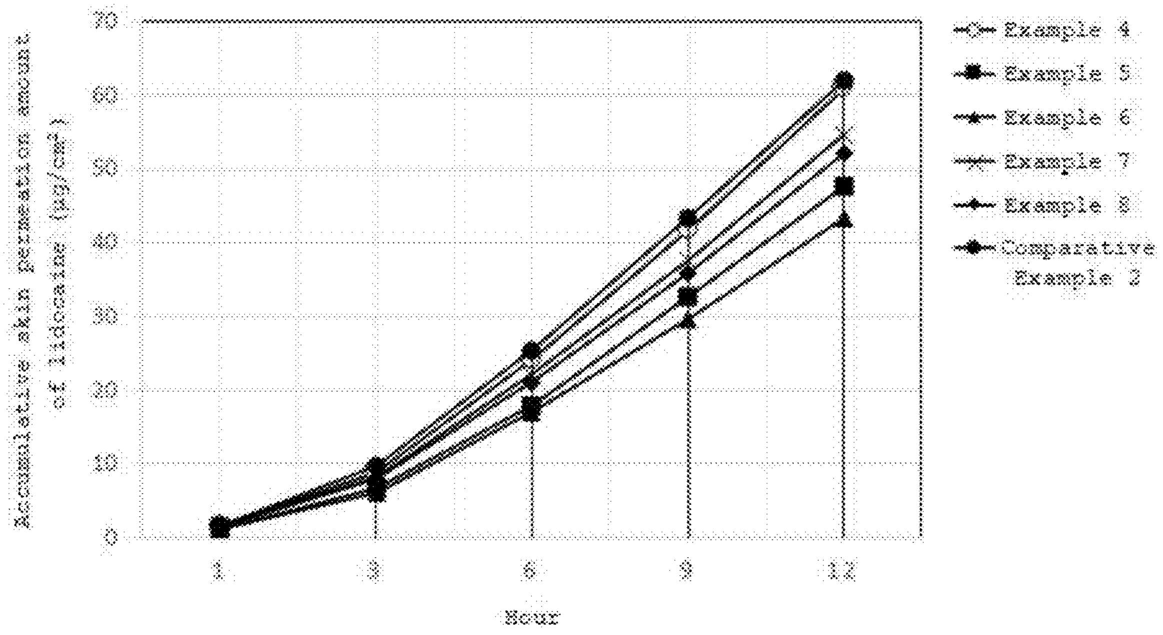
[Fig. 4]
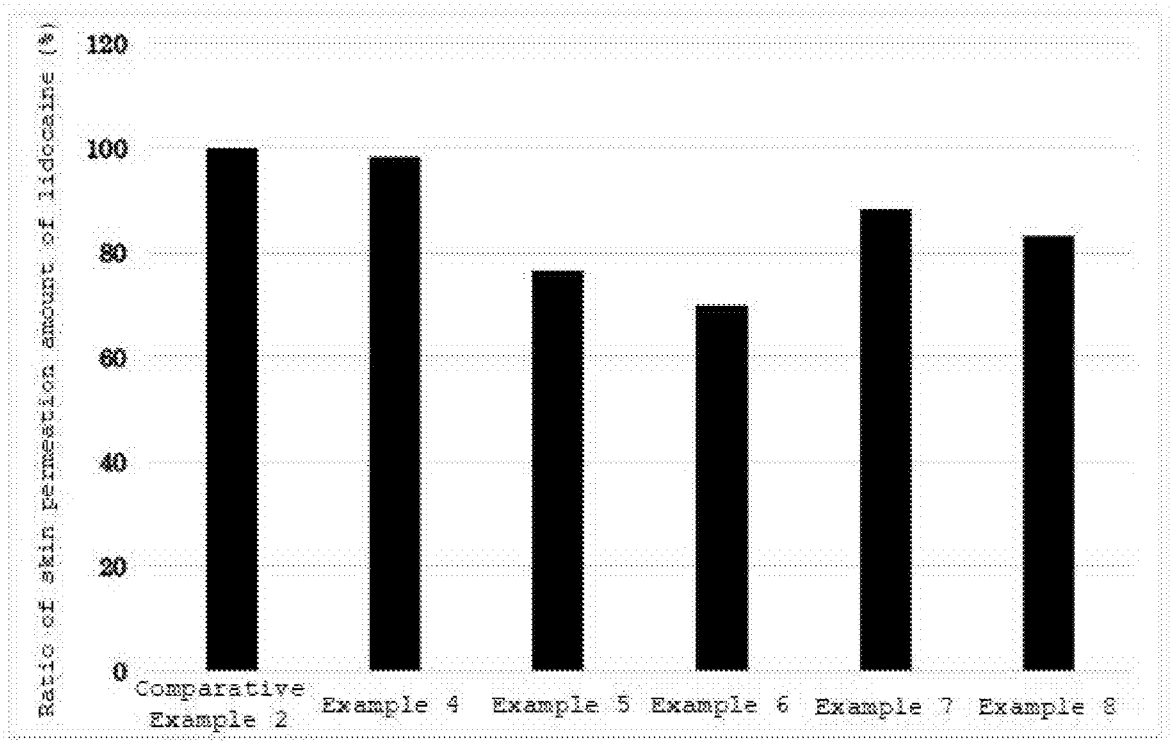

[Fig. 5]
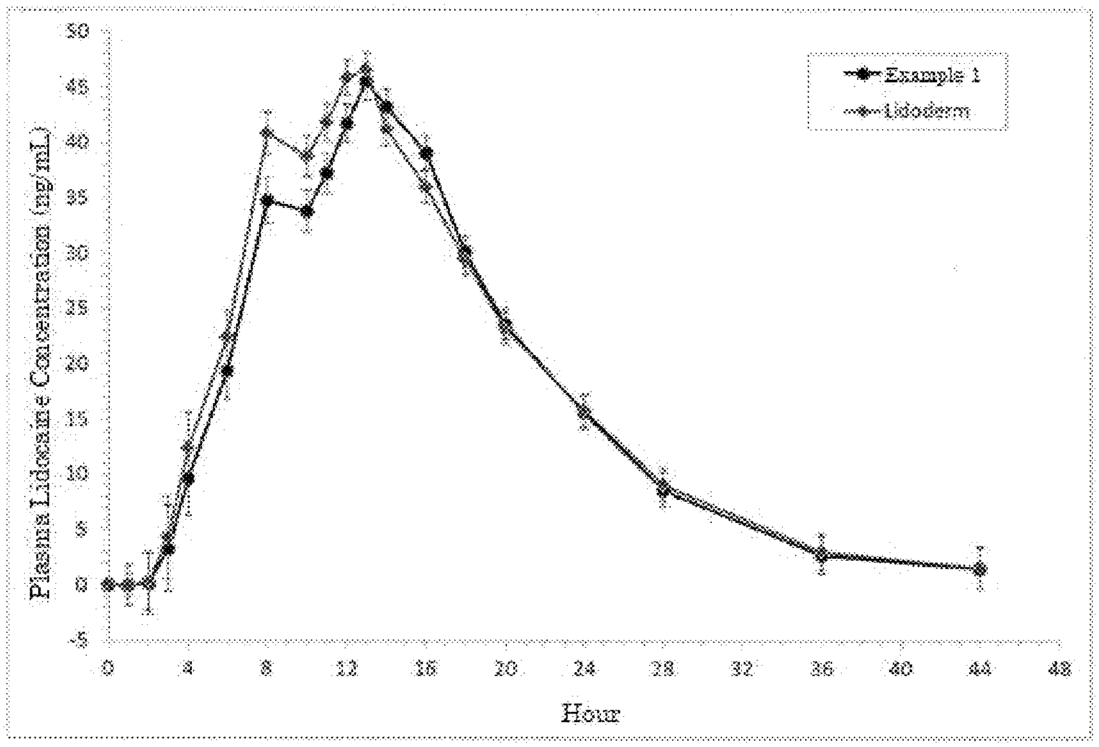
[Fig. 6]
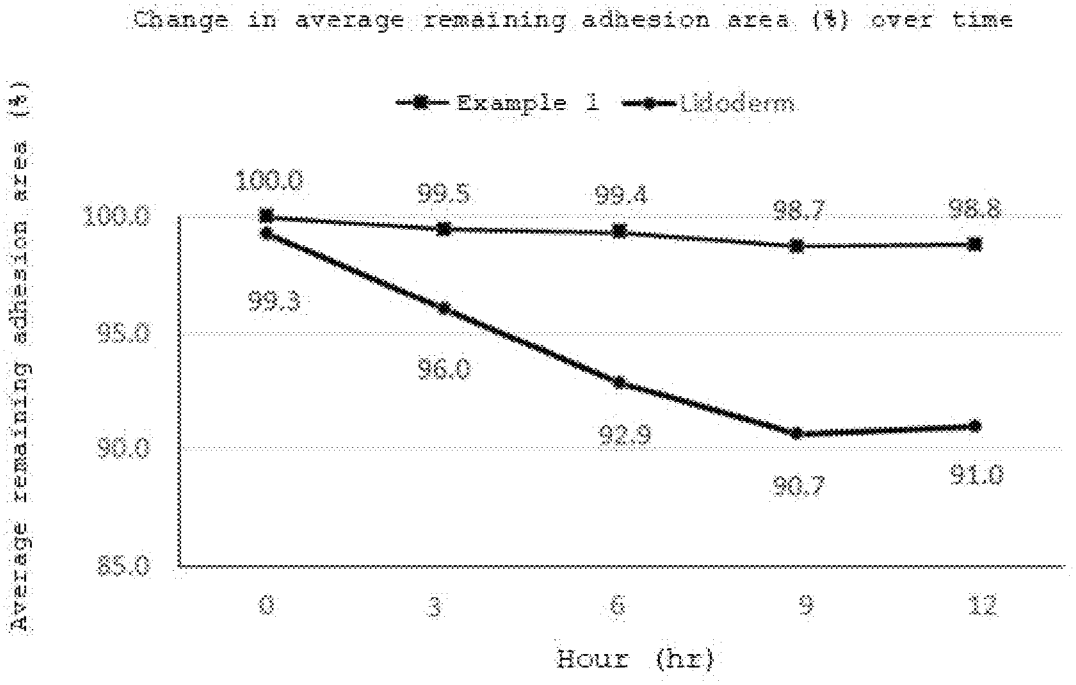

[Fig. 7]
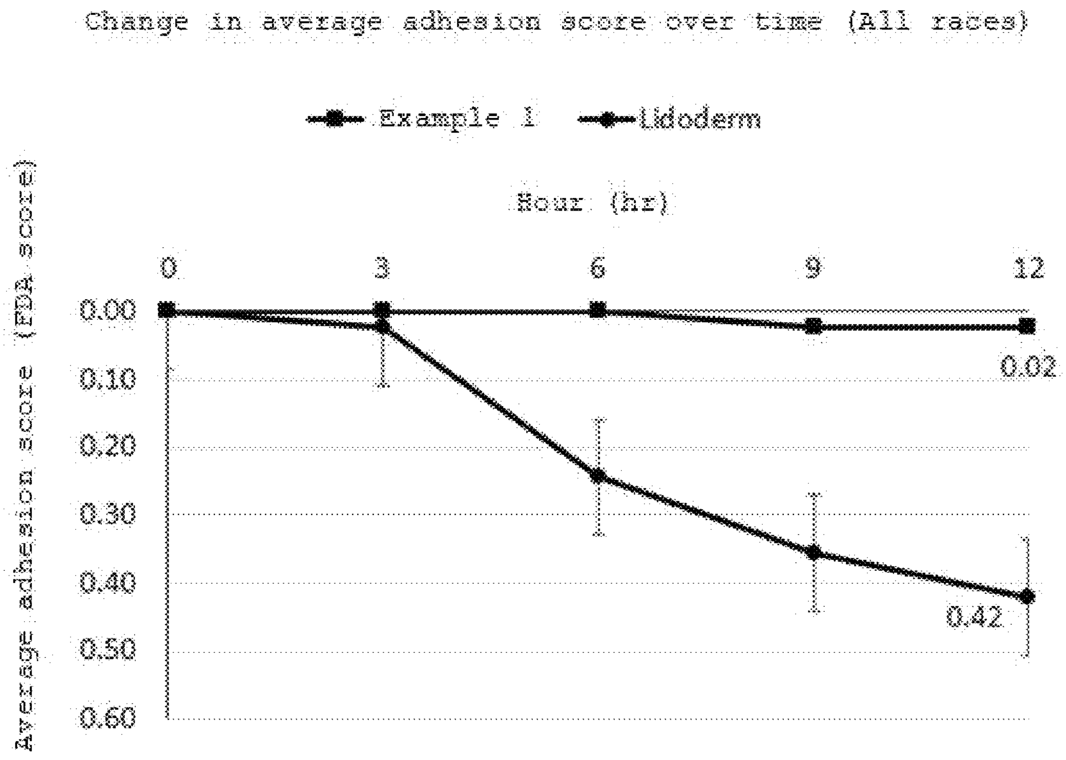

LIDOCAINE-CONTAINING PATCH

TECHNICAL FIELD

The present invention relates to a patch preparation comprising lidocaine, more specifically a patch preparation comprising lidocaine or a salt thereof, lactic acid, and a hydroxy acid having 4 to 6 carbon atoms wherein the amount of lactic acid is 0.6 to 1.2 moles per mole of lidocaine or a salt thereof.

BACKGROUND ART

For lidocaine which is a local anesthetic, various external preparations comprising it have been studied so far, and some patch preparations comprising lidocaine as an active ingredient have been commercially available. For example, in US, Lidoderm® (cataplasm comprising 5% lidocaine) and ZTlido® (Tape preparation comprising 1.8% lidocaine) have been commercially available.

The patch preparations comprising lidocaine had a problem. Specifically, in the patch preparations, the undissolved lidocaine was dispersed in the adhesive layer by the precipitation of the crystals of lidocaine in the adhesive layer, and thus sufficient amount of lidocaine was not absorbed in the body even when applied to the skin and the effect of lidocaine was not sufficiently produced. For the skin permeability, it has been reported that the skin permeability of lidocaine is enhanced by reacting lidocaine and lactic acid in equimolar amounts to form an equimolar salt of lidocaine-lactic acid in the form of ionic liquid (cf. Patent Document 1). However, Patent Document 1 focuses on enhancing the skin permeability of lidocaine, and does not disclose or suggest that lidocaine can continuously penetrate the skin.

In addition, it has been known that lidocaine is a drug that affects the heart, and causes any side effects such as shock, redness and feeling of stimulation or lidocaine toxicity when high concentration of lidocaine is used for a long time. Hence, when high concentration of lidocaine is added into a preparation, it was necessary to demonstrate that the preparation is biologically equivalent to existing preparations, for example, Lidoderm® to ensure the effectiveness and safety of the preparation.

For example, Patent Document 2 discloses that a drug can continuously penetrate the skin for a long time by controlling the amount of each ingredient for an adhesive layer and arranging the mass (thickness) of the adhesive layer to be within the predetermined range. However, in the preparation of Patent Document 2, the amount of the local anesthetic (lidocaine) to be added is adjusted to low concentration and it is not used at high concentration.

Also, it has not been reported that a preparation comprising lidocaine can produce the same skin permeability and adhesibility as preparations comprising lidocaine at low concentration and achieve more continuous absorption of lidocaine even when lidocaine is used at high concentration by the use of lidocaine or a salt thereof and lactic acid in a specific molar ratio as well as a hydroxy acid having 4 to 6 carbon atoms.

PRIOR ART DOCUMENTS

Patent Documents

Patent Document 1: WO 2009/060629
Patent Document 2: WO 2018/052039

SUMMARY OF INVENTION

Problem to be Solved by the Invention

For a patch preparation, when 30-40% of a drug contained in a plaster (adhesive layer) is absorbed to the skin, the absorption rate of the drug is reduced. As a result, the drug cannot be continuously absorbed. When higher concentration of the drug is added in the plaster, the drug can be continuously absorbed for a long time as compared to when low concentration of the drug is used.

On the other hand, it is found that a preparation comprising lidocaine prepared by a usual method, for example, a preparation comprising lidocaine prepared by the method of Patent Document 2 (hot melt method) comprises an organic acid such as tartaric acid and can control the amount of lidocaine absorbed. However, since an organic acid with small molecular weight (e.g., tartaric acid) is highly water soluble, the organic acid could not be added in the amount required to form a salt with lidocaine into a plaster comprising a lipophilic base when the concentration of lidocaine is increased. As a result, lidocaine is presented in the free form with high crystallinity without forming a salt with an organic acid in the plaster, and lidocaine in the free form causes the problem of precipitating the crystals of lidocaine during long-term storage. Hence, it was necessary to adjust the concentration of lidocaine to low concentration in a preparation comprising lidocaine and an organic acid with small molecular weight. That is, such preparation had any problem to achieve the continuous absorption of lidocaine for a long time. In addition, the use of high concentration of lidocaine for a long time causes lidocaine toxicity, and thus there was the large problem that the effectiveness and safety of a preparation is ensured even when the concentration of lidocaine is increased.

The present invention has been studied considering the above situation, and an object of the present invention is to provide a patch preparation comprising lidocaine with high safety which can continuously produce the therapeutic effect of lidocaine for a long time by adjusting the skin penetration rate of lidocaine to a proper range when applied to the skin and also show the similar bioequivalence to the existing preparations comprising lidocaine even when high concentration of lidocaine is used. Also, an object of the present invention is to prevent the precipitation of the crystals of lidocaine and produce the feature that is hard to be removed during exercising without reducing the adhesion to the skin.

Means for Solving the Problems

The present inventors have succeeded that the skin permeability of lidocaine in a patch preparation comprising lidocaine is improved by forming an equimolar salt of lidocaine and lactic acid (an ionic liquid) and keeping lidocaine in the dissolved state even when high concentration of lidocaine is contained in the tape plaster. On the other hand, the present inventors have considered the need for reducing the skin permeation amount of lidocaine per hour and adjusting the skin permeation rate of lidocaine to a proper range when the preparation is used for a long time. The present inventors have found that although the skin permeation amount of lidocaine can be controlled in any methods for reducing the amount of lidocaine to be added, the continuous skin permeation of lidocaine for a long time may be lost when the amount of lidocaine to be added is added in low. Based upon the findings, the present inventors have also found that it is necessary to suitably control the skin permeation amount of lidocaine while maintaining high concentration of lidocaine. The present inventors tried to control the skin permeation amount of lidocaine by adding a hydroxy acid having 4 to 6 carbon atoms (e.g., tartaric acid) into an equimolar salt of lidocaine and lactic acid, but the object could not be reached because the hydroxy acid was not dissolved. The present inventors have extensively studied to reach the object, and have succeeded that a mixture of lactic acid and tartaric acid is preliminarily prepared in a specific amount and then lidocaine is added thereto in a specific molar ratio to prepare a uniform composition. In addition, the present inventors have found that a patch preparation comprising the resulting composition can properly control the skin permeation rate of lidocaine, produce good skin permeability and adhesibility, and assure the bioequivalence with Lidoderm® which has been commercially available in US. Based upon the new findings, the present invention has been completed.

That is, the present invention provides the following aspects.

[1] A patch preparation comprising lidocaine or a salt thereof, lactic acid and a hydroxy acid having 4 to 6 carbon atoms, wherein the amount of lactic acid is 0.6 to 1.2 moles per mole of lidocaine or a salt thereof.

[2] The patch preparation of the item [1], wherein the hydroxy acid having 4 to 6 carbon atoms is citric acid or tartaric acid.

[3] The patch preparation of the item [1] or [2], wherein the hydroxy acid having 4 to 6 carbon atoms is tartaric acid.

[4] The patch preparation of any one of the items [1] to [3], wherein the amount of lactic acid is 1.0 to 1.2 moles per mole of lidocaine or a salt thereof.

[5] The patch preparation of any one of the items [1] to [4], wherein the amount of lidocaine or a salt thereof is 5 to 50%.

[6] The patch preparation of any one of the items [1] to [5], wherein the amount of lidocaine or a salt thereof is 10 to 40%.

[7] The patch preparation of any one of the items [1] to [6], wherein the amount of lidocaine or a salt thereof is 10 to 20%.

[8] The patch preparation of any one of the items [1] to [7], wherein the amount of the hydroxy acid having 4 to 6 carbon atoms is 0.2 to 5%.

[9] The patch preparation of any one of the items [1] to [8], wherein the amount of the hydroxy acid having 4 to 6 carbon atoms is 0.3 to 0.8%.

[10] The patch preparation of any one of the items [1] to [9] comprising a support, an adhesive layer and a release liner, wherein the adhesive layer comprises lidocaine or a salt thereof, lactic acid and a hydroxy acid having 4 to 6 carbon atoms.

[11] The patch preparation of the item [10], wherein the adhesive layer further comprises an ester.

[12] The patch preparation of the item [11], wherein the ester is diethyl sebacate, methyl laurate, diisopropyl adipate, isopropyl myristate, propylene carbonate or a mixture thereof.

[13] The patch preparation of any one of the items [10] to [12], wherein the adhesive layer further comprises a surfactant.

[14] The patch preparation of the item [13], wherein the surfactant is a non-ionic surfactant with a HLB value of 4 to 14.

[15] The patch preparation of any one of the items [10] to [14], wherein the adhesive layer further comprises an elastomer.

[16] The patch preparation of the item [15], wherein the elastomer is styrene-isoprene-styrene block copolymer (SIS).

[17] The patch preparation of any one of the items [10] to [16], wherein the thickness of the patch preparation is 0.50 to 2.00 mm.

[18] The patch preparation of any one of the items [10] to [17], wherein the surface area of the adhesive layer is 100 to 200 $cm^2$.

[19] A method for manufacturing the patch preparation of any one of the items [1] to [18], which comprises:

(a) mixing lactic acid in an amount of 0.6 to 1.2 moles per mole of lidocaine or a salt thereof with a hydroxy acid having 4 to 6 carbon atoms; and (b) adding lidocaine or a salt thereof to the mixture in the above (a) to prepare a uniform composition.

In addition, the present invention provides the following aspects.

[20] A method for treating pain which comprises administering a therapeutically effective amount of the patch preparation of any one of the items [1] to [18] to a patient in need thereof.

[21] The patch preparation of any one of the items [1] to [18] for the use in treating pain.

[22] Use of the patch preparation of any one of the items [1] to [18] in the manufacture of a medicament for treating pain.

Effects of the Invention

The present invention can adjust the skin penetration rate of lidocaine when applied to the skin to a proper range and continuously produce the therapeutic effect of lidocaine for a long time. In addition, the present invention can assure the bioequivalence with the existing patch preparations comprising lidocaine even when higher concentration of lidocaine is used, and thus can maintain the therapeutic effect of lidocaine for a long time as compared to the existing patch preparations comprising lidocaine and reduce the risk of side effects caused by the use of the preparations for a long time.

The patch preparation of the present invention can maintain the adhesion to the skin without precipitating the crystals of lidocaine in the adhesive layer, and thus can be used during exercise. In addition, the patch preparation can ensure the safety against the use of the preparation for a long time, and thus is expected to reduce the number of administration.

BRIEF DESCRIPTION OF THE DRAWINGS

FIG. 1 shows a graph representing the accumulative skin permeation amounts of lidocaine (μg/$cm^2$) in the preparations of Examples 1-3 and Comparative Example 1 in in vitro skin permeation test.

FIG. 2 shows the ratios of the skin permeation amounts of lidocaine (%) in the preparations of Examples 1-3 when the skin permeation amount of lidocaine in the preparation of Comparative Example 1 is defined as 100%.

FIG. 3 shows a graph representing the accumulative skin permeation amounts of lidocaine (μg/$cm^2$) in the preparations of Examples 4-8 and Comparative Example 2 in in vitro skin permeation test.

FIG. 4 shows the ratios of the skin permeation amounts of lidocaine (%) in the preparations of Examples 4-8 when the skin permeation amount of lidocaine in the preparation of Comparative Example 2 is defined as 100%.

FIG. 5 shows a graph representing the average profile of plasma concentration versus time after the preparation of Example 1 (n=32) and Lidoderm® (n=28) are applied to human back (mean±standard deviation).

FIG. 6 shows the changes in the average remaining adhesion area (%) over time of the preparation of Example 1 (n=45) and Lidoderm® (n=45).

FIG. 7 shows the changes in the average adhesion score over time of the preparation of Example 1 (n=45) and Lidoderm® (n=45).

DETAILED DESCRIPTION OF THE PREFERRED EMBODIMENTS

As used herein, "lidocaine" may be in the free form or a salt form thereof. The salt of lidocaine includes a salt with an inorganic acid and a salt with an organic acid, but is not limited thereto.

Examples of the salt with an inorganic acid include hydrochloride, hydrobromide, nitrate, and phosphate, and examples of the salt with an organic acid include acetate, trifluoroacetate, propionate, oxalate, fumarate and maleate.

As used herein, lidocaine or a salt thereof is preferably used as lidocaine (in the free form).

The amount of lidocaine or a salt thereof may be 1 to 50% by weight, 5 to 50% by weight, 5 to 45% by weight, 10 to 50% by weight, 10 to 40% by weight, 10 to 35% by weight, 10 to 30% by weight, 10 to 25% by weight, 10 to 20% by weight or 10 to 15% by weight relative to the total amount of the preparation, but is not limited thereto. Also, the amount thereof may be 1% by weight, 2% by weight, 3% by weight, 4% by weight, 5% by weight, 6% by weight, 7% by weight, 8% by weight, 9% by weight, 10% by weight, 11% by weight, 12% by weight, 13% by weight, 14% by weight, 15% by weight, 16% by weight, 17% by weight, 18% by weight, 19% by weight, 20% by weight, 25% by weight, 30% by weight, 35% by weight, 40% by weight, 45% by weight or 50% by weight.

As used herein, lidocaine (in the free form) can form an ion pair with lactic acid to prepare lactic acid salt of lidocaine in the preparation, and also can be prepared as a salt with a hydroxy acid having 4 to 6 carbon atoms, for example, citric acid or tartaric acid.

As used herein, "lactic acid" involves in the formation of an ion pair with an equimolar amount of lidocaine to prepare lactic acid salt of lidocaine (equimolar salt).

As used herein, the amount of lactic is 0.6 to 1.2 moles, and preferably 1.0 to 1.2 moles per mole of lidocaine or a salt thereof.

As used herein, "lactic acid salt of lidocaine" is an ionic liquid (an ambient temperature molten salt) produced by forming an ion pair of lidocaine and lactic acid in equimolar amounts, and is in the viscous liquid form at ambient temperature.

The amount of lactic acid salt of lidocaine may be, for example, 1 to 50% by weight, and the amount thereof may be 5 to 50% by weight, 10 to 50% by weight, 10 to 40% by weight, 10 to 35% by weight, 10 to 30% by weight, 10 to 20% by weight or 10 to 15% by weight. Also, the amount of lactic acid salt of lidocaine may be 1% by weight, 2% by weight, 3% by weight, 4% by weight, 5% by weight, 6% by weight, 7% by weight, 8% by weight, 9% by weight, 10% by weight, 11% by weight, 12% by weight, 13% by weight, 14% by weight, 15% by weight, 20% by weight, 25% by weight, 30% by weight, 35% by weight, 40% by weight, 45% by weight or 50% by weight.

Lactic acid salt of lidocaine can be prepared as an equimolar salt of lidocaine and lactic acid by mixing lidocaine and lactic acid in the presence or absence of solvent and heating (for example, at 80° C.). Also, lactic acid salt of lidocaine can be prepared by mixing lidocaine and lactic acid at room temperature.

As used herein, lactic acid salt of lidocaine may be prepared as an equimolar salt by the reaction of a part of lidocaine and a part of lactic acid. Hence, unreacted lidocaine and lactic acid may be contained in a preparation.

As used herein, the "hydroxy acid having 4 to 6 carbon atoms" means a carboxylic acid with straight or branched hydroxyl group(s) which has 4 to 6 carbon atoms. Examples thereof include tartaric acid and citric acid, but are not limited thereto.

The amount of the hydroxy acid having 4 to 6 carbon atoms may be 0.1 to 10% by weight, 0.2 to 5% by weight, 0.25 to 4% by weight, 0.25 to 3% by weight, 0.3 to 2% by weight, 0.3 to 1% by weight, 0.3 to 0.8% by weight, 0.35 to 0.8% by weight or 0.4 to 0.8% by weight relative to the total amount of the preparation, but is not limited thereto. Also, the amount thereof may be 0.1% by weight, 0.15% by weight, 0.2% by weight, 0.25% by weight, 0.3% by weight, 0.35% by weight, 0.4% by weight, 0.45% by weight, 0.5% by weight, 0.55% by weight, 0.6% by weight, 0.65% by weight, 0.7% by weight, 0.75% by weight, 0.8% by weight, 0.85% by weight, 0.9% by weight, 0.95% by weight, 1% by weight, 1.1% by weight, 1.2% by weight, 1.3% by weight, 1.4% by weight, 1.5% by weight, 1.6% by weight, 1.7% by weight, 1.8% by weight, 1.9% by weight, 2% by weight, 2.5% by weight, 3% by weight, 3.5% by weight, 4% by weight, 4.5% by weight, 5% by weight, 5.5% by weight, 6% by weight, 6.5% by weight, 7% by weight, 7.5% by weight, 8% by weight, 8.5% by weight, 9% by weight, 9.5% by weight or 10% by weight.

The patch preparation of the present invention may comprise a surfactant, an alcohol, an ester, a carbolic acid (excluding a hydroxy acid having 4 to 6 carbon atoms) and an amine, if necessary. They may be used alone or two or more of them may be used in combination.

Examples of the surfactant include a non-ionic surfactant, an anionic surfactant, a cationic surfactant, and an amphoteric surfactant. The surfactant may be used alone or two or more of the surfactants may be used in combination.

Examples of the non-ionic surfactant include sorbitan monolaurate, sorbitan monopalmitate, sorbitan sesquioleate, glycerol monooleate, glycerol monostearate, decaglyceryl monolaurate, hexaglycerin polyricinoleate, polyoxyethylene (9) lauryl ether, polyoxyethylene (2) lauryl ether, polyoxyethylene (4,2) lauryl ether, polyoxyethylene (5) nonylphenyl ether, polyoxyethylene (7,5) nonylphenyl ether, polyoxyethylene (10) nonylphenyl ether, polyoxyethylene (3) octylphenyl ether, polyoxyethylene (10) octylphenyl ether, polyoxyethylene (10) oleylamine, polyoxy (5) oleylamine, polyoxy (5) oleic acid amide, polyoxyethylene (2) monolaurate, monoglyceride stearate, and polyoxyethylene castor oil (hydrogenated castor oil), but are not limited thereto. The non-ionic surfactant may be used alone or two or more of the non-ionic surfactants may be used in combination.

Examples of the anionic surfactant include sodium lauryl sulfate, potassium lauryl sulfate, triethanolamine lauryl sulfate, sodium cetyl sulfate, lauroylsarcosine sodium, sodium di-2-ethylhexyl sulfosuccinate, sodium polyoxyethylene (10) lauryl ether phosphate, sodium polyoxyethylene (4) lauryl ether phosphate, sodium polyoxyethylene (5) cetyl ether phosphate, and sodium polyoxyethylene (6) oleyl ether phosphate, but are not limited thereto. The anionic surfactant may be used alone or two or more of the anionic surfactants may be used in combination.

Examples of the cationic surfactant include stearyl trimethyl ammonium chloride, distearyl dimethyl ammonium chloride, benzalkonium chloride and stearyl dimethylbenzyl ammonium chloride, but are not limited thereto. The cationic surfactant may be used alone or two or more of the cationic surfactants may be used in combination.

Examples of the amphoteric surfactant include lauryl dimethyl aminoacetic acid betaine and 2-alkyl-N-carboxymethyl-N-hydroxyethylimidazolinium betaine, but are not limited thereto. Lauroyl diethanolamide can also be used as the amphoteric surfactant other than the above surfactant. The amphoteric surfactant may be used alone or two or more of the amphoteric surfactants may be used in combination.

The surfactant of the present invention is preferably a surfactant with a HLB value of 4 to 14, more preferably a surfactant with a HLB value of 4 to 14 comprising one or more non-ionic surfactants, and furthermore preferably a surfactant with a HLB value of 6-12 comprising monoglyceride stearate and polyoxyethylene castor oil (hydrogenated castor oil).

The amount of the surfactant is, for example, 0.01 to 2% by weight, and preferably 0.01 to 1% by weight.

Examples of the alcohol include a lower alcohol such as ethanol, propanol, isopropylalcohol and butanol; a higher alcohol such as lauryl alcohol, myristyl alcohol, oleyl alcohol, isostearyl alcohol and cetyl alcohol; a dihydric alcohol such as ethylene glycol, propylene glycol, butanediol (1,3-butanediol, 1,4-butanediol), pentanediol and hexanediol; a trihydric alcohol such as glycerin and hexanetriol; and an aromatic alcohol such as glycol salicylate and benzyl alcohol. The alcohol of the present invention is preferably propylene glycol, 1,3-butanediol and glycerin. The alcohol may be used alone or two or more of the alcohols may be used in combination.

The amount of the alcohol is, for example, 0.01 to 2% by weight, and preferably 0.01 to 1% by weight.

Examples of the ester include isopropyl isostearate, methyl stearate, butyl myristate, ethyl linoleate, isopropyl linoleate, ethyl olivate, myristyl myristate, cetyl isooctanoate, octyldodecyl myristate, diisopropyl adipate, cetyl palmitate, retinol palmitate, methyl laurate, methyl myristate, methyl caproate, methyl palmitate, isopropyl myristate, isopropyl palmitate, diethyl sebacate, diethyl adipate, glycerin monooleate, glycerin monocaproate, glycerin dioleate, propylene glycol monostearate, decaglycerin decaoleate, sorbitan monostearate, sorbitan monolaurate, sorbitan monooleate, sorbitan trioleate, ascorbyl palmitate, n-propyl gallate, diisopropyl adipate, propylene carbonate, and a pyrrolidone derivative such as N-methyl-2-pyrrolidone, but are not limited thereto. The ester of the present invention is preferably isopropyl myristate, isopropyl palmitate, diethyl sebacate, propylene carbonate and N-methyl-2-pyrrolidone, and furthermore preferably propylene carbonate and N-methyl-2-pyrrolidone. The ester may be used alone or two or more of the esters may be used in combination.

The amount of the ester is, for example, 0.01 to 2% by weight, and preferably 0.01 to 1% by weight.

Examples of the carboxylic acid include a fatty acid such as oleic acid, palmitic acid, succinic acid, lauric acid, myristic acid, stearic acid, isostearic acid and decanoic acid; and a keto acid such as levulinic acid, but are not limited thereto. The carboxylic acid may be used alone or two or more of the carboxylic acids may be used in combination.

The amount of the carboxylic acid is, for example, 0.01 to 2% by weight, and preferably 0.01 to 1% by weight.

Examples of the amine include monoethanolamine, diethanolamine, isopropanolamine, triethanolamine, triisopropanolamine, ethylenediamine and trishydroxymethylaminomethane, but are not limited thereto. The amine may be used alone or two or more of the amines may be used in combination.

The amount of the amine is, for example, 0.01 to 2% by weight, and preferably 0.01 to 1% by weight.

In the patch preparation of the present invention, when the total amount of the alcohol, the ester, the carboxylic acid and the amine exceeds 30% by weight, the adhesive layer may be soften. As a result, it is sometimes difficult to prepare the patch preparation.

The patch preparation of the present invention may be in the form of three-layer structure composed of a support, an adhesive layer comprising lidocaine or a salt thereof, and a release liner. For example, the patch preparation may be in the form of the structure in which the adhesive layer is laminated on the one side of the support and the release liner is laminated on the surface of the adhesive layer opposite the surface that adheres to the support.

The patch preparation of the present invention comprises lidocaine, lactic acid and a hydroxy acid having 4 to 6 carbon atoms in the adhesive layer. In addition, an agent such as a surfactant, a surfactant, an alcohol, an ester, a carboxylic acid (excluding a hydroxy acid having carbon atoms of 4 to 6) and an amine are contained in the adhesive layer.

The patch preparation of the present invention comprises a suitable elastomer (polymer) in the adhesive layer.

The patch preparation of the present invention can be prepared as a matrix-type patch preparation by dispersing a solution comprising lidocaine or a salt thereof in an adhesive layer comprising an elastomer. When the patch preparation of the present invention is such matrix-type patch preparation, the amount of lactic acid salt of lidocaine may be 1 to 50% by weight, 10 to 50% by weight, 10 to 40% by weight, 10 to 35% by weight, 10 to 30% by weight, 10 to 20% by weight or 10 to 15% by weight relative to the total amount of the dried adhesive layer.

The elastomer of the present invention includes a rubber polymer, an acrylic polymer, a silicon polymer and a vinyl ether polymer, but is not limited thereto. The elastomer may be used alone or two or more of the elastomers may be used in combination.

Examples of the rubber polymer include a synthetic rubber such as styrene-isoprene-styrene block copolymer (hereinafter, also referred to as "SIS"), styrene-butadiene-styrene block copolymer, styrene-ethylene-butadiene rubber-styrene block copolymer, styrene-butadiene rubber, polyisoprene, polyisobutylene, polybutene, butyl rubber, silicone rubber; and a natural rubber, but are not limited thereto.

Examples of the acrylic polymer include acrylic acid-octyl acrylate ester copolymer, 2-ethylhexyl acrylate-vinylpyrrolidone copolymer, 2-ethylhexyl acrylate-N-vinyl-2-pyrrolidone-1,6-hexaneglycol dimethacrylate copolymer, acrylate-vinyl acetate copolymer and 2-ethylhexyl acrylate-2-hydroxyethyl acrylate-vinyl acetate copolymer, but are not limited thereto.

Examples of the silicon polymer include silicon rubber, dimethylpolysiloxane and diphenylpolysiloxane, but are not limited thereto.

In the patch preparation of the present invention, the adhesive layer may further comprise an additive such as a tackifier, a softener, a filler and an anti-oxidant.

Examples of the tackifier include rosin, rosin ester resin, hydrogenated rosin ester, terpene resin, terpene phenolic resin, C5 type petroleum resin, C5/C9 type petroleum resin, DCPD (dicyclopentadiene) type petroleum resin, coumarone-indene resin, alicyclic saturated hydrocarbon resin. The tackifier may be used alone or two or more of the tackifiers may be used in combination.

The amount of the tackifier is, for example, 0.01 to 50% by weight, preferably 10 to 40% by weight, and furthermore preferably 20 to 40% by weight.

Examples of the softener include a petroleum-based softener such as process oil and polybutene, a fatty oil-based softener such as castor oil and coconut oil, purified lanolin, liquid paraffin, and gelled hydrocarbon, but are not limited thereto. The softener may be used alone or two or more of the softeners may be used in combination.

The amount of the softener is, for example, 0.01 to 50% by weight, preferably 10 to 40% by weight, and furthermore preferably 20 to 40% by weight.

Examples of the filler include kaolin, titanium oxide, talc, calcium carbonate, magnesium carbonate, silicate, silicic acid, aluminum hydrate, barium sulfate, and calcium sulfate, but are not limited thereto. The filler can adjust the adhesive layer to an appropriate hardness when the adhesive layer becomes too flexible.

The amount of the filler is, for example, 0.01 to 5% by weight and preferably 0.01 to 3% by weight.

Examples of the anti-oxidant include dibutyl hydroxy toluene (BHT), butylated hydroxyanisole (BHA), propyl gallate, ascorbic acid, sodium sulfite, sodium hydrogen sulfite, and sodium pyrosulfite, but are not limited thereto. The anti-oxidant may be used alone or two or more of the anti-oxidants may be used in combination.

The amount of the anti-oxidant is, for example, 0.01 to 2% by weight, and preferably 0.01 to 1% by weight.

As the support in the patch preparation of the present invention, a drug-impermeable and stretchable or unstretchable support can be used. The support is not particularly limited thereto as long as it is generally used in the pharmaceutical field. Examples thereof include polyethylene, polypropylene, polybutadiene, ethylene-vinyl acetate copolymer, polyvinyl chloride, polyester (such as polyethylene terephthalate), synthetic resin film or sheet or laminated product thereof, porous material, foam, film with deposited aluminum, paper, woven cloth, and non-woven cloth.

In the patch preparation of the present invention, the release liner can be used to protect the adhesive layer until the preparation is applied to the skin. As the packaging material for packaging the preparation of the present invention, an aluminum laminated film can be used. The material such as polyacrylonitrile, a polyethylene terephthalate and polyethylene can be used in the innermost layer of the aluminum laminated film.

The patch preparation of the present invention can be prepared by any well-known methods such as the solvent coating method and the hot melt coating method.

Examples of the solvent coating method include a method which comprises preparing a composition for adhesive layer comprising lactic acid salt of lidocaine and the like, coating the composition directly onto a support and then drying. Also, a method, which comprises coating the composition for adhesive layer onto a release paper and drying, removing the paper, and then contact pressing the adhesive layer onto a support, can be used. Examples of the hot melt coating method include a method which comprises heat melting the composition for adhesive layer, coating the composition directly onto a support and then drying. Also, a method, which comprises heat melting the composition for adhesive layer, coating the composition onto a release paper and drying, removing the paper, and then contact pressing the adhesive layer onto a support, can be used as the hot melt coating method.

In addition, the composition for adhesive layer in the patch preparation of the present invention can be prepared by mixing each ingredient in the adhesive layer and then stirring them. For example, a composition for adhesive layer can be prepared by dissolving an elastomer and a tackifier in toluene, adding other additive such as a surfactant and a solvent such as an ester thereto and mixing with heating, dissolving the mixture, and then adding lidocaine, lactic acid and a hydroxy acid having 4 to 6 carbon atoms thereto and stirring them. Lidocaine may be added into the mixture solution produced by mixing lactic acid and a hydroxy acid having 4 to 6 carbon atoms.

As used herein, the thickness of the patch preparation is preferably about 0.50 to about 2.00 mm, and more preferably about 0.55 to about 1.00 mm. The thickness thereof may be, for example, about 0.50 mm, about 0.51 mm, about 0.52 mm, about 0.53 mm, about 0.54 mm, about 0.55 mm, about 0.56 mm, about 0.57 mm, about 0.58 mm, about 0.59 mm, about 0.60 mm, about 0.61 mm, about 0.62 mm, about 0.63 mm, about 0.64 mm, about 0.65 mm, about 0.66 mm, about 0.67 mm, about 0.68 mm, about 0.69 mm, about 0.70 mm, about 0.71 mm, about 0.72 mm, about 0.73 mm, about 0.74 mm, about 0.75 mm, about 0.76 mm, about 0.77 mm, about 0.78 mm, about 0.79 mm, about 0.80 mm, about 0.85 mm, about 0.90 mm, about 0.95 mm, about 1.00 mm, about 1.10 mm, about 1.20 mm, about 1.30 mm, about 1.40 mm, about 1.50 mm, about 1.60 mm, about 1.70 mm, about 1.80 mm, about 1.90 mm or about 2.00 mm.

When the thickness of the patch preparation, particularly the thickness of the adhesive layer in the patch preparation is increased without changing the amount of lidocaine, the concentration of lidocaine is reduced. As a result, the absorption amount of lidocaine can be controlled. On the other hand, some problems may be caused, for example, a large amount of an adhesive may be attached to the skin when the patch preparation is removed, and the solvent contained in the adhesive layer may enhance the skin stimulation.

As used herein, the surface area of the adhesive layer in the patch preparation is preferably 100 to 200 $cm^2$, more preferably 120 to 180 $cm^2$, and furthermore preferably 130 to 160 $cm^2$. In addition, as used herein, the amount of lactic acid salt of lidocaine per unit area of the adhesive layer is, for example, 1 to 5 $mg/cm^2$, preferably 1 to 2 $mg/cm^2$, and more preferably 1 to 1.5 $mg/cm^2$.

The patch preparation of the present invention can maintain the adhesion to the skin without precipitating the crystals of lidocaine in the adhesive layer. The patch preparation of the present invention is hard to be removed even during exercising, and thus can be used during exercise.

The number of administrations of the patch preparation of the present invention varies with the patient's symptoms and age, but the number thereof is preferably once a day, once in every two days, once in every three days or once a week, and more preferably once a day for an adult. The number thereof can be increased depending on the symptoms.

The patch preparation of the present invention is used for the treatment or relief of various types of pain such as neuropathic pain in the depth of the skin (e.g., postherpetic neuralgia), cervico-omo-brachial syndrome and migraine derived from the trigeminal nerve.

As used herein, the term "treatment (treating)" means every treatment of pain or the associated symptoms, for example, treating or improving pain and alleviating or inhibiting symptoms with pain. The treatment also encompasses inhibiting recurrence of pain.

As used herein, the term "patient" means human and an animal such as dog, cat, horse. Among them, the patient is preferably human.

As used herein, the term "therapeutically effective amount" means any amount for treating, improving and/or alleviating pain and the symptoms thereof as compared to untreated patients. The term also includes any effective amount for promoting normal physiological function with the range.

EXAMPLES

Hereinafter, the present invention is described more specifically with reference to Examples and Test Examples. However, the present invention is not intended to be limited to them by any means.

Examples 1 to 3

Each ingredient was weighed in the amounts shown in Table 1 below, and the patch preparations of Examples 1 to 3 were prepared. Specifically, according to the solvent method, styrene-isoprene-styrene block copolymer (SIS) and terpene resin were dissolved in toluene, and then glycerin monostearate, polyoxylethylene hydrogenated castor oil 40, propylene carbonate and gelled hydrocarbon were added thereto and mixed with heating, and the mixture was dissolved to prepare an adhesive layer. Separately, lactic acid (Purity: 90%) and tartaric acid were mixed, and to the mixture solution was added lidocaine to prepare a uniform composition. The composition was mixed with the above adhesive layer to prepare a uniform composition for adhesive layer. The resulting composition for adhesive layer was coated onto the silicone-treated PET film and dried to remove toluene, and then the obtained plaster was laminated onto a support and cut to the 10 cm×14 cm size to prepare a patch preparation.

TABLE 1

| | Example 1 | Example 2 | Example 3 |
|---|---|---|---|
| Lidocaine | 10% | 10% | 10% |
| Lactic Acid | 5% | 5% | 5% |
| Tartaric Acid | 0.4% | 0.6% | 0.8% |
| Glycerin Monostearate | 0.008% | 0.008% | 0.008% |
| Polyoxyethylene Hydrogenated Castor Oil 40 | 0.017% | 0.017% | 0.017% |
| Propylene Carbonate | 1% | 1% | 1% |
| Gelled Hydrocarbon | 38.575% | 38.375% | 38.175% |
| SIS | 10% | 10% | 10% |
| Terpene Resin | 35% | 35% | 35% |
| Total | 100% | 100% | 100% |

Comparative Example 1

Each ingredient was weighed in the amounts shown in Table 2 below, and the preparation of Comparative Example 1 was prepared according to a similar procedure to the preparations of Examples 1 to 3, except that tartaric acid is not added.

TABLE 2

| | Comparative Example 1 |
|---|---|
| Lidocaine | 10% |
| Lactic Acid | 5% |
| Tartaric Acid | — |
| Glycerin Monostearate | 0.008% |
| Polyoxyethylene Hydrogenated Castor Oil 40 | 0.017% |
| Propylene Carbonate | 1% |
| Gelled Hydrocarbon | 38.975% |
| SIS | 10% |
| Terpene Resin | 35% |
| Total | 100% |

Test Example 1: Study for Skin Permeability of Lidocaine by Addition of Hydroxy Acid Having 4 to 6 Carbon Atoms (1)

According to the following procedure, the skin permeation amounts of lidocaine in the preparations of Examples 1 to 3 and Comparative Example 1 were measured.

A Franz cell was set and was filled with saline. The Franz cell was warmed at around 32° C. A disc with a φ15 mm hole in a φ24 mm membrane filter was attached on the back side of the thawed skin of a miniature pig, the skin was punched with a φ24 mm punch, and the skin was set in the Franz cell. The excess water around the Franz cell and on the upper surface of the skin was wiped off. The skin was acclimated to the environment for about 20 minutes and then was removed. Each preparation punched to φ12 mm was applied to the central part of the skin, and the skin was set in the Franz cell. The excess water around the Franz cell was wiped off, the filter paper punched to φ24 mm was placed on the skin, and the cap of the Franz cell was closed and fixed with a clip. The sampling of each preparation was performed 1 hr, 2.5 hr, 6 hr, 9 hr and 12 hr after the start of the test, and the skin permeation amounts thereof were measured by high performance liquid chromatography (HPLC). The amounts were calculated as the average value (n=3).

The accumulative skin permeation amounts of lidocaine after 1 hr, 2.5 hr, 6 hr, 9 hr and 12 hr (μg/cm$^2$) in the preparations are shown in Table 3 and FIG. 1. In addition, the ratios of the skin permeation amounts of lidocaine in the preparations of Examples 1 to 3 to the skin permeation amount of lidocaine in the preparation of Comparative Example 1 after 12 hr (%) are shown in FIG. 2.

TABLE 3

| | Example 1 | Example 2 | Example 3 | Comparative Example 1 |
|---|---|---|---|---|
| Accumulative skin permeation amount after 1 hr | 1.81 | 1.39 | 2.62 | 2.65 |
| Accumulative skin permeation amount after 2.5 hr | 9.25 | 7.47 | 11.05 | 14.85 |
| Accumulative skin permeation amount after 6 hr | 31.79 | 23.55 | 28.56 | 46.56 |
| Accumulative skin permeation amount after 9 hr | 55.48 | 42.73 | 47.20 | 80.62 |
| Accumulative skin permeation amount after 12 hr | 76.55 | 59.81 | 63.22 | 108.26 |

It was demonstrated that the skin permeation amount of lidocaine could be reduced by the addition of tartaric acid (Table 3 and FIGS. 1-2).

Test Example 2: Study for Skin Permeability of Lidocaine by Addition of Hydroxy Acid Having 4 to 6 Carbon Atoms (2)

The skin permeability of each preparation comprising lidocaine which comprises tartaric acid or citric acid as a hydroxy acid having 4 to 6 carbon atoms was studied.

Each ingredient was weighed in the amounts shown in Table below. The preparations of Examples 4 to 8 were prepared according to a similar procedure to the preparations of Examples 1 to 3, and the preparation of Comparative Example 2 was prepared according to a similar procedure to the preparation of Comparative Example 1. The skin permeation amounts of lidocaine in the preparations of Examples 4 to 8 and Comparative Example 2 were measured in a similar procedure to Test Example 1, except that Strat-M® membrane (manufactured by Merck) was used in place of the skin of a miniature pig and the sampling was performed 1 hr, 3 hr, 6 hr, 9 hr and 12 hr after the start of the test. The amounts were calculated as the average value (n=3).

TABLE 4

| | Example 4 | Example 5 | Example 6 | Example 7 | Example 8 | Comparative Example 2 |
|---|---|---|---|---|---|---|
| Lidocaine | 10% | 10% | 10% | 10% | 10% | 10% |
| Lactic acid | 5% | 5% | 5% | 5% | 5% | 5% |
| Tartaric acid | 0.2% | 0.4% | 0.5% | — | — | — |
| Citric acid | — | — | — | 0.2% | 0.4% | — |
| Glycerin monostearate | 0.008% | 0.008% | 0.008% | 0.008% | 0.008% | 0.008% |
| Polyoxyethylene hydrogenated castor oil | 0.017% | 0.017% | 0.017% | 0.017% | 0.017% | 0.017% |
| Propylene carbonate | 1% | 1% | 1% | 1% | 1% | 1% |
| Gelled hydrocarbon | 38.775% | 38.575% | 38.475% | 38.775% | 38.975% | 38.975% |
| SIS | 10% | 10% | 10% | 10% | 10% | 10% |
| Terpene resin | 35% | 35% | 35% | 35% | 35% | 35% |
| Total | 100% | 100% | 100% | 100% | 100% | 100% |

The accumulative skin permeation amounts of lidocaine after 1 hr, 3 hr, 6 hr, 9 hr and 12 hr (μg/cm$^2$) in the preparations are shown in Table 5 and FIG. 3. In addition, the ratios of the skin permeation amounts of lidocaine in the preparations of Examples 4 to 8 to the skin permeation amount of lidocaine in the preparation of Comparative Example 2 after 12 hr (%) are shown in FIG. 4.

TABLE 5

| | Example 4 | Example 5 | Example 6 | Example 7 | Example 8 | Comparative Example 2 |
|---|---|---|---|---|---|---|
| Accumulative skin permeation amount after 1 hr | 1.57 | 1.258 | 1.121 | 1.713 | 1.478 | 1.716 |
| Accumulative skin permeation amount after 3 hr | 9.015 | 6.744 | 6.145 | 8.358 | 8.14 | 9.839 |
| Accumulative skin permeation amount after 6 hr | 24.235 | 17.915 | 16.992 | 22.193 | 21.236 | 25.467 |
| Accumulative skin permeation amount after 9 hr | 41.751 | 32.657 | 22.193 | 37.633 | 35.824 | 43.466 |
| Accumulative skin permeation amount after 12 hr | 61.029 | 47.6 | 43.394 | 54.721 | 52.128 | 62.082 |

It was demonstrated that the skin permeation amount of lidocaine could be controlled by the addition of not only tartaric acid but also citric acid (Table 4 and FIGS. 3-4).

Test Example 3: In Vivo Pharmacokinetic Study of Preparation of the Present Invention and Existing Preparation (Lidoderm®)

According to the following procedure, the concentrations of lidocaine in plasma of the preparation of Example 1 and the patch preparation comprising lidocaine sold in US (Lidoderm®) were measured. Also, each preparation was pharmacokinetically analyzed to evaluate the bioequivalence with the existing preparation.

32 healthy persons (Male and Female, 19 to 65 years old) per group were enrolled as subjects. Two sheets of either Lidoderm or the preparation of Example 1 (Size: 10 cm×14 cm) were applied to the back of each subject and they were removed from the back 12 hours after the application of the preparations. Blood was collected at the time of 1, 2, 3, 4, 6, 8, 10, 11, 12, 13, 14, 16, 18, 20, 24, 28, 36 and hours after each preparation is applied, and the concentration of lidocaine in plasma was measured with LC/MS/MS. Also, the non-compartmental pharmacokinetic analysis was performed based on the change in the concentration of lidocaine in plasma using Phoenix WinNonlin Version 7.0 to calculate the AUC (area under the blood concentration time curve) and the $C_{max}$ (maximum blood concentration). In addition, the geometric mean ratios of the AUC and the $C_{max}$ in the preparation of Example 1 and Lidoderm® were calculated. 4 subjects to which Lidoderm® was applied were excluded from the study because the applied preparation was removed during the study.

The change in the concentration of lidocaine in plasma (mean±standard deviation) are shown in FIG. 5. The calculated AUC and $C_{max}$ are shown in Table 6. The 90% confidence intervals for the geometric mean ratios of the AUC and the $C_{max}$ were within an acceptable range of 80%-125%.

TABLE 6

| | Lidoderm (n = 28) | Example 1 (n = 32) | Geometric mean ratio for Lidoderm ® |
|---|---|---|---|
| $AUC_{0-t}$ (ng*hr/mL) | 797.3 | 759.2 | 95.22 |
| $AUC_{0-inf}$ (ng*hr/mL) | 823.7 | 780.6 | 94.77 |
| $C_{max}$ (ng/mL) | 50.05 | 48.62 | 97.14 |

It was confirmed that the preparation of Example 1 showed the almost same pharmacokinetic (PK) profile as Lidoderm® (Table 6 and FIG. 5). That is, it was shown that the preparation of present invention is biologically equivalent to Lidoderm®.

Also, the lidocaine utilization rate at the time of 12 hours after the preparation is applied to the skin was 29%. Hence, it is shown that about 70% lidocaine is remained in the preparation, and thus the preparation can be continuously used. That is, the preparation of the present invention can continuously produce the therapeutic effect of lidocaine for a long time as compared to Lidoderm®.

Test Example 4: Adhesion Test of the Preparation of the Present Invention and Existing Preparation (Lidoderm®)

According to the following procedure, an adhesion test of the preparation of Example 1 and the patch preparation comprising lidocaine sold in US (Lidoderm®) for human was performed to measure the remaining adhered area (%). In addition, according to the FDA guidance (Assessing Adhesion With Transdermal and Topical Delivery Systems for ANDAs Guidance for Industry (DRAFT GUIDANCE) October 2018), the adhesion scores were calculated for each preparation (0: ≥90% adhered 1: ≥75% to <90% adhered, 2: ≥50% to <75% adhered, 3: >0% to <50% adhered, 4: 0% adhered) to assess the adhesion durability of the preparations.

45 healthy persons (Male and Female of all races) per group were enrolled as subjects. 1 sheet of the patch preparation (Size: 10 cm×14 cm) or 1 sheet of Lidoderm® were applied to the back of each subject. The adhered site at each subject was set to be anatomically equivalent. The average remaining adhesion area (%) and average adhesion score were calculated at the time of 3, 6, 9 and 12 hours after the start of the test to assess the adhesion durability of the preparations.

The changes in the average remaining adhesion area (%) over time of each preparation are shown in FIG. 6. In addition, the changes in the average adhesion score over time of each preparation are shown in FIG. 7.

In the preparation of the present invention, 44 subjects had adhesion scores of 0 and 1 subject had an adhesion score of 1, out of 45 subjects, at the time of 12 hours after the preparation is applied. Hence, it was shown that the preparation of the present invention was hard to be removed for a long time and had the feature that is hard to be removed even during exercising.

INDUSTRIAL APPLICABILITY

The present invention can adjust the skin penetration rate of lidocaine when applied to the skin to a proper range and continuously produce the therapeutic effect of lidocaine for a long time. In addition, the present invention can assure the bioequivalence with existing patch preparations comprising lidocaine even when lidocaine is contained in a higher concentration, and thus can maintain the therapeutic effect of lidocaine for a long time as compared to the existing patch preparations comprising lidocaine and reduce the risk of side effects caused by the use of the preparations for a long time.

The patch preparation of the present invention can maintain the adhesion to the skin without precipitating lidocaine crystals in the adhesive layer, and thus can be used during exercise. In addition, the patch preparation can ensure the safety against the use of the preparation for a long time, and thus is expected to reduce the number of administration.

The invention claimed is:

1. A method for manufacturing a patch preparation comprising an adhesive layer comprising lidocaine or a salt thereof, lactic acid, a hydroxy acid selected from the group consisting of citric acid and tartaric acid, and an elastomer wherein the elastomer comprises styrene-isoprene-styrene block copolymer (SIS), the method comprising:

(a) mixing lactic acid in an amount of 0.6 to 1.2 moles per mole of lidocaine or a salt thereof with the hydroxy acid in an amount of 0.3 to 0.8% by weight of the adhesive layer to form a first mixture;

(b) adding lidocaine or a salt thereof in an amount of 10 to 20% by weight of the adhesive layer to the first mixture to form a second mixture; and (c) preparing an elastomer mixture by generating a third mixture by dissolving SIS and terpene resin in toluene, generating a fourth mixture by adding to the elastomer mixture glycerin monostearate, polyoxyethylene hydrogenated castor oil 40, propylene carbonate, and gelled hydrocarbon and mixing with heat, and dissolving the fourth mixture; and (d) adding the elastomer mixture to the second mixture to prepare a uniform composition.

2. The method of claim 1, wherein the hydroxy acid is citric acid.

3. The method of claim 1, wherein the hydroxy acid is tartaric acid.

4. The method of claim 1, wherein the amount of lactic acid is 1.0 to 1.2 moles per mole of the lidocaine or the salt thereof.

5. The method of claim 1, wherein the glycerin monostearate, polyoxyethylene hydrogenated castor oil 40, propylene carbonate, and gelled hydrocarbon are mixed with heat.

6. The method of claim 1, wherein the lactic acid and the hydroxy acid are mixed before the lidocaine or the salt thereof is added.

7. The method of claim 6, wherein the lidocaine or the salt thereof is added to the mixture of the lactic acid and the hydroxy acid.

8. The method of claim 1, wherein the adhesive layer further comprises one or more tackifiers comprising at least one selected from the group consisting of rosin, rosin ester resin, hydrogenated rosin ester, terpene phenolic resin, C5 petroleum resin, C5/C9 petroleum resin, DCPD petroleum resin, coumarone-indene resin, and alicyclic saturated hydrocarbon resin.

9. The method of claim 8, wherein the one or more tackifiers are present in an amount of 10 to 40% by weight of the adhesive layer.

10. The method of claim 1, wherein the adhesive layer further comprises one or more softeners comprising at least one selected from the group consisting of process oil, polybutene, castor oil, coconut oil, purified lanolin, liquid paraffin, and gelled hydrocarbon.

11. The method of claim 10, wherein the one or more softeners are present in an amount of 10 to 40% by weight of the adhesive layer.

12. The method of claim 1, wherein the adhesive layer further comprises a surfactant.

13. The method of claim 12, wherein the surfactant is a non-ionic surfactant with a HLB value of 4 to 14.

* * * * *